(12) United States Patent
Landesberg et al.

(10) Patent No.: US 6,322,785 B1
(45) Date of Patent: Nov. 27, 2001

(54) METHODS AND COMPOSITIONS FOR BONE GRAFT IMPLANTS

(75) Inventors: Regina Landesberg, Stamford, CT (US); Glenn Morris Gainey, New York, NY (US)

(73) Assignee: Natrex Technologies, Greenville, NC (US)

( * ) Notice: Subject to any disclaimer, the term of this patent is extended or adjusted under 35 U.S.C. 154(b) by 0 days.

(21) Appl. No.: 09/261,291

(22) Filed: Mar. 2, 1999

(51) Int. Cl.$^7$ ........................................... A01N 63/00
(52) U.S. Cl. .................................. 424/93.72; 514/21
(58) Field of Search ............................. 424/93.72; 514/21

(56) References Cited

U.S. PATENT DOCUMENTS 6,096,309 * 8/2000 Prior et al. .

OTHER PUBLICATIONS

Kemp et al., "Preparation of an alkali–soluble collagen from demineralized bone", Biochem. J. 134 (5): 915–19 (1971).*

Babloyan et al., "Some structural and biochemicl features of the products of enzymic and alkali–salt dissolution of mature fibrillar collagen", J. Polym. Sci., Polym. Symp. 69: 43–8 (1981).*

* cited by examiner

Primary Examiner—Sandra E. Saucier
(74) Attorney, Agent, or Firm—Susanne M Hopkins

(57) ABSTRACT

An autologous platelet gel for bone grafts is comprised of a mixture of platelet-rich-plasma activated by calcium chloride solution, and an aqueous suspension of partially frayed Type I collagen.

8 Claims, No Drawings

METHODS AND COMPOSITIONS FOR BONE GRAFT IMPLANTS

FIELD OF INVENTION

The present invention relates to methods and compositions for bone repair and, in particular, an implantable, thrombin-free, autologous platelet gel and matrix that promotes bone augmentation and regeneration.

BACKGROUND OF THE INVENTION

Fibrin glue, also known as fibrin sealant or fibrin gel, is one of many materials developed in response to a recognized need for improved hemostatic agents and sealant (Ref. 1). Platelet-based implantable gels have been used extensively as wound healing and bone regeneration agents in preferred substitution for fibrin glues. Fibrin glues are a two component system comprising, as a first component, concentrated fibrogen, a fibrin stabilizing factor and fibroconectin. The second component includes thrombin, calcium chloride, and an inhibitor of fibrinolysis. The constituents when combined form a fibrin gel or clot. Thrombin and the calcium cleave the fibrogen to fibrin in the coagulation cascade and activate factor XIII which crosslinks fibrin into an organized clot. The gel may be topically applied or in-vitro molded prior to implantation.

The fibrogen content is customarily plasma based. Such plasma may be derived from a variety of sources including random donor or single-donor cryoprecipitate or from autologous plasma. Homologous sourcing presents numerous quality control problems. Procured from donor blood, certain patient risks may be encountered including compatibility problems, disease transmission dangers, clerical and storage errors. While an autologous cryoprecipitate overcomes some of the above, the donor blood must be procured substantially in advance of surgery, 3 to 5 days or more.

Autologous platelet gel was developed in further response to the above. Therein, whole blood is obtained from the patient in the preoperative period and processed in the operating area. Through differential centrifugation, a fraction representing the platelet strata is separated. This strata or platelet-rich-plasma (PRP) is combined with thrombin and calcium chloride representatively using the technique set forth in Whitman et. al, Ref. 1 above. It has also been proposed that such resultant clots be supplemented with calcium phosphate minerals and other osseoparticulates including autologous bone and marrow material for use in oral and maxillofacial surgery.

Autologous platelet gel differs from fibrin glue in the presence of a high concentration of platelets and a high concentration of native fibrogen. The platelets, activated by the thrombin, release factors and form scaffolding for the development of a clot. Two of the growth factors, platelet derived growth factor (PDGF) and transforming growth factor-beta (TGF-B) are known to promote wound healing. PDGF is an activator of collangenase during wound healing allowing reshaping of collagen for wound strength. It also is known to be chemotactic for monocytes and macrophages. TGF-B is known to activate fibroblasts to form procollagen resulting in collagen deposition within the wound.

Autologous platelets gels have gained acceptance in the area of reconstructive oral surgery in connection with ablative surgery of the maxillofacial region, mandibular reconstruction, surgical repair of alveolar clefts and associated oral-antral/oral-nasal fistulas, and adjunctive procedures related to the placement of osseointegrated implants. Such platelet gels have also been used in combination with particulate cancellous bone and marrow grafts (PCBM) (Ref. 1, Ref. 2). It is reported that such platelet gels with the graft material evidenced substantially greater maturation rates and bone density than such implants without the platelet-rich-plasma. The PDGF and TGF growth factors were amplified in this approach and the probable primary initiators of the results.

The action of the thrombin in such autologous platelet gels has been recognized as the primary biological release mechanism of these growth factors as discussed in U.S. Pat. No. 5,165,938 to Knighton. While other biological release agents such as collagen, ADP, and srotonin have been suggested for activating, the performance of thrombin was preferred and appears to have been adopted in the art as the agent of choice. The thrombin customarily used in both platelet gels and fibrin systems has been a bovine derivative. To reduce potential xenographic effects, the bovine thrombin has been used in highly purified form.

Notwithstanding the improved results reported with the thrombin-based fibrin and platelet systems, there are numerous reports detailing adverse clinical effects that have been linked potentially to the bovine thrombin. Sosolik et. al. reported a prolongation of thrombin time was associated with the presence of anti-bovine thrombin antibodies following surgical procedures when fibrin glues or bovine thrombin preparations were applied topically and it was suggested that such exposure could lead to serious bleeding complications during surgery or the postoperative period (Ref. 3). Spero concluded that bovine-induced coagulopathy may occur following surgical exposure to topical bovine thrombin and may result in both postoperative morbidity and mortality in a subset of patients resulting from topical-induced antibodies to clotting factor V following neurolosurgical procedures (Ref. 4). Cmolik et. al. reports coagulopathy occasioned by bovine thrombin-induced factor V deficiency after exposure to bovine thrombin in topical hemostatic agents during cardiovascular or vascular operation (Ref. 5). Muntean et. al. reported inhibitors to factor V following exposure to fibrin sealant during cardiac surgery and concluded that exposure to topical thrombin preparations may lead to the development of inhibitors in the postoperative period that may cause bleeding complications (Ref. 6). Based on the foregoing and other reports, Landsberg et. al. cautioned against use of bovine topical thrombin-based platelet gels in oral and maxilofacial procedures and expressed the need for alternative methods of activating PRP in the oral surgery area (Ref. 7).

BRIEF SUMMARY OF THE INVENTION

The present invention provides an autologous platelet gel and bone graft matrix that is thrombin-free and promotes osteoconduction, osteoinduction and osteogenesis at a bone augmentation site, and initiates and augments the bone replacement process. The implant compositions of the present invention comprise an admixture of platelet-rich-plasma, osseoparticulates, a gelling initiator, and a osseoinductive carrier comprising a suspension of terminally defribillated fibrillar collagen. The admixture is in-vitro cured to form a gelled composition that is formable for implantation into bone deficient sites. Osseoparticluates in a variety of forms can be utilized as the osseocondutive medium including autologous bone and marrow, allographic bone particulate, xenographic particulate bone substitutes and other calcium phosphate minerals. The collagen suspension is a microfibrillar Type I collagen processed to undergo partial unwinding of the collagen strands at the ends thereof sufficient to maintain suspension in a physiological medium and effective to act as a carrier for the scaffolding and as an osseogenetic promoter.

REFERENCES. The publications set forth above are hereby incorporated by reference.

1. "Platelet Gel: An autologous Alternative to Fibrin Glue with Applications in Oral and Maxilofacial Surgery", Whitman, D H et al., J. Oral Maxilofacial Surgery, 1294–1299 (1997).
2. "Platelet-rich plasma: Growth factor enhancement for bone grafts", Mars, R E et al., Oral Surg Oral Med Oral Pathol Oral Radiol Endod, Vol. 85, 638–646, (1998).
3. "Anti-Bovine Thrombin Antibody", Sosolik, R C et al., Laboratory Medicine, Vol. 27, No. 10, 651–653 (1998).
4. "Bovine thrombin-induced inhibitor of factor V and bleeding risk in postoperative neurosurgical patients", Spero J A, J Neurosurg, Vol 78, 817–820 (1993).
5. "Redo cardiac surgery: Late bleeding complications from topical thrombin-induced factor V deficiency", Cmolik, B L, J Thorac Cardiovasc Surg, Vol 105, 222–228 (1993).
6. "Inhibitor to factor V after exposure to fibrin sealant during cardiac surgery in a two-year-old child", Muntean, W, Acta Paediar, Vol. 83, 84–87 (1994).
7. "Risks of using platelet-rich-plasma gel", Landesberg, R, J Oral Maxilofac Surg, Vol. 56, 1116–1117 (1998).

DESCRIPTION OF PREFFERED EMBODIMENTS

The autologous platelet gel and matrix of the present invention is produced using patient derived platelet-rich-plasma fraction derived from preoperative donated blood. For use as an autologous platelet sealant/bone graft matrix, the composition comprises by volume about 10 to 60 parts of platelet-rich-plasma; 1 to 5 parts calcium chloride; 5 to 60 parts of partially defibrillated Type I collagen; and 5 to 40 parts osseoparticulate. Such composition is made by: forming initially a mixture of alkaline induced terminally frayed Type I fibrillar collagen and water; adjusting the mixture to a pH in the range of about 8 to 12; stirring said mixture at said range for a time sufficient to establish a stable suspension; readjusting the suspension to a pH in the physiological range; combining the suspension with calcium chloride solution as an activator system; and combining the activator system with autologous platelet-rich-plasma under time and temperature conditions yielding a clotted, formable gel, supplemented in accordance with the application by osseoparticulate.

The procedure for harvesting the platelet-rich-plasma may be practiced in many variations, however, the procedure as described in Marx (Ref. 2) may be beneficially used herein. Such procedure involves obtaining from the prospective implant patient, immediately preoperative, whole blood, which is transferred into a collection reservoir containing a citrate-phosphate-dextrose anticoagulant. The anticoagulated whole blood is transferred to a centrifuge for separation at about 5600 rpm into plural layers comprising: platelet-poor-plasma, upper layer: erythrocytes, lower layer; and the "buffy coat", middle layer, containing the platelet-rich-plasma fraction. The platelet-poor-plasma, upper layer fraction, is removed by aspiration and the remainder recentrifuged at 2400 rpm to further define the remaining fractions. The buffy coat middle layer containing the platelet-rich-plasma is removed and stored at room temperature for future use. Such technique is reported to yield 500,000 to 1,000,000 platelets in the PRP from a unit of whole blood.

While the foregoing separation procedure produces generally acceptable results, the present invention has determined that greater yield and improved morphology can be obtained by more gently sequestering the platelets. Herein, a sample of whole blood is transferred to a centrifuge tube containing a suitable coagulant such as citrate solution. The tube is centrifuged in the range of 175 g to 300 g for a period of time, 5 to 15 minutes, sufficient to delineate the sample into three distinct layers; a top layer containing platelet poor plasma, a buffy coat middle layer containing platelet-rich-plasma, and a lower layer containing the red blood cells. Thereafter, the top and middle layers are transferred to a second centrifuge tube. The tube is centrifuged again at a gentle speed in the range of 200 g to 300 g for a period of time, generally 5 to 15 minutes, sufficient to delineate clearly the upper layer of platelet-poor-plasma and the now lower layer containing the platelet-rich-plasma. The layers are thereafter separated, and the platelet-rich-plasma reserved for use. Such gentle sequestration of the platelet-rich-plasma has been found to produce increased yields of intact platelets exhibiting a morphology substantially unaffected by the separation process.

The gelling initiator or clotting activator is an inorganic solution compatible with the graft constituents for effecting gelling or clotting of the autologous platelet gel and matrix. For the collagen-based system of the present invention a calcium chloride aqueous solution is preferred.

The carrier and osseoinductive constituent and second constituent of the activator is preferably a Type I fibrillar collagen derived from allographic or xenographic sources. Type I Bovine collagen is preferred, however, other suitable animal sources such as mammalian or avian may be used. The collagen is alkaline treated to promote strand uncurling at the ends of the fibers. Such processing permits the collagen to form a stable aqueous suspension. Thereafter, the suspension is neutralized to physiological conditions for use in the gel and platelet compositions as hereinafter described.

EXAMPLE 1

Preparation of Conventional Thrombin-Based Platelet Gel

Platelet-rich-plasma was obtained as set forth above. In a mixing bowl, 1 ml of platelet-rich-plasma, 60 ul of 0.91M calcium chloride, and 10,000U of Type 1 bovine thrombin were mixed to form a moldable viscous clot with the consistency of a gel.

EXAMPLE 2

Preparation of Collagen-based Platelet Gel

In a mixing bowl, 1 ml of platelet-rich-plasma, 60nl of 0.91M calcium chloride and 0.5 ml of collagen suspension (1 mg/ml) made in accordance with example 3 below were thoroughly mixed and transferred to a heating surface maintained at 37° C. for about 10 minutes until a viscous gel was formed.

EXAMPLE 3

Preparation of Collagen Suspension

A collagen suspension was prepared by admixing 0.5 grams of fibrillar Type I Bovine Collagen (J&J Medical Systems, Product No 1984) in 5 ml of distilled water. The pH of the mixture was increased to 10.2 with the addition of 10M Sodium Hydroxide. The adjusted mixture was gently stirred for a period of 8 hours at which time the collagen remained in stable suspension. The adjusted suspension was neutralized to physiologic conditions at a pH of 7.2 by the addition or 10M hydrochloric acid. Microscopic examination of the collagen fibers indicated frayed termini on the fiber ends resultant from above processing.

EXAMPLE 4

Determination of PDGF and TGF-B Content

In order to determine the effects of the thrombin-based gel as prepared in accordance with Example 1 and the collagen-based gel of the present invention as prepared in accordance with Example 2 in the release of Platelet Derived Growth Factor (PDGF) and Transforming Growth Factor-Beta (TGF-B), 10 ml samples based on different blood sources were analyzed in accordance with established protocols The results are set forth below in Table A

TABLE A

|  | Sample | | |
| --- | --- | --- | --- |
|  | A | B | C |
| PDGF (Units) | | | |
| Thrombin | 157.3 | 113.7 | 107.4 |
| Collagen | 155.4 | 127.7 | 130.3 |
| TGF-B (Units) | | | |
| Thrombin | 118.0 | 123.9 | 154.7 |
| Collagen | 111.9 | 130.9 | 169.21 |

The foregoing demonstrates that both gel preparations are substantially equally effective in releasing the noted growth factors associated with bone and tissue augmentation.

EXAMPLE 5

Gel Conditions

To illustrate the effect of time, temperature and calcium chloride concentration on clotting time and consistency, three samples of gels in accordance with Example 2 above were prepared with the exceptions that two samples used the 10% calcium chloride and one sample an equal volume of 2M solution. The 10% samples clotted at room temperature in 11.5 minutes and at 37° C. in 4 and 4.5 minutes. The 2M solution did not clot at either temperature.

EXAMPLE 6

Clot Consistency

To illustrate the effect of calcium chloride concentration on the collagen-based platelet gel, three samples of the gel were prepared in accordance with Example 2 in the following proportions:

| Sample | A | B | C |
| --- | --- | --- | --- |
| PRP | 100 ml | 100 ml | 100 ml |
| Calcium Chloride | 14 ml | 50 ml | 6 ml |
| Collagen | 20 ml | 50 ml | 100 ml |
| Clotting Time | no clot | no clot | 7.6 min |

Such conditions indicated that increased amounts of the calcium chloride adversely affected the desired clotting characteristics, even in the presence of temperature activation.

EXAMPLE 7

Preparation of Platelet Gel for Implantation

The collagen suspension prepared in Example 5, 10 ml was mixed in a sterile glass bowl with 10 ml of 0.91M calcium chloride. The collagen mixture was then mixed with 50 ml. of plasma rich platelets contained in a second glass container and mixed until evenly distributed. Preliminary gelling was noted. The glass container was placed on a hot plate maintained at 37° C. for clotting. After 30 minutes of heating, the resultant platelet gel was removed and found to be uniformly clotted and readily moldable into retentive shapes conformal to an implant site.

EXAMPLE 8

Preparation Platelet Augmentation Osteograph Composition

Prior to heating, 25 mg. of cadavillar particulate bone was added to the ungelled mixture and mixed until well incorporated. The resultant mixture in the glass container was placed on a hot plate maintained at 37° C. for gellation. After 30 minutes of heating, platelet gel with particulate was removed and bound to be readily moldable into typical dental implant shapes.

EXAMPLE 9

Implantation of Osteograph Composition

A quantity of composition prepared in accordance with Example 8 was preliminary molded and inserted into a mandibular void of a subject. The composition was further defined to desired shape. The surrounding tissue was then closed by sutures. Visual inspection during the postoperative period did not indicate any inflammation or swelling attributable to the implant. Subsequent visual and radiological observation indicated progressive increase in both load-bearing and complete osteointegration in accordance with conventional analysis. No allergic or antibody reaction was noted for a period of up to 4 months. At the end of 5 months, the implant was fully integrated and load supporting.

The bone graft material of the present invention has application in craniofacial reconstruction, periodontal defects, joint reconstruction, fracture repair, orthopedic surgical procedures, spinal fusion, bone defects, odontolological defects in osteoconductive/osteoinductive grafting applications.

The gel matrices of the present invention also have applications in any surgical or invasive technique in which manipulative or promotion of wound tissue deficit healing is intended.

The gels and matrices of the present invention also have application as matrices for the storage and encapsulation of cellular moieties such as pancreatic islets, xenographic or allographic, hepatocytic cells and the like.

Various modifications of the invention in addition to those described herein will become apparent to those skilled in the art from the foregoing description. Such modifications are intended to be within the scope of the appended claims.

What is claimed is:

1. A formable platelet gel, comprising: an aqueous suspension of partially frayed Type I fibrillar collagen; calcium chloride; and autologous platelet-rich-plasma, said formable platelet gel does not contain thrombin.

2. A formable platelet gel, comprising: an aqueous suspension of Type I fibrillar collagen, which has been alkali treated to create partially frayed termini; calcium chloride; and autologous, platelet-rich-plasma, which has been processed to produce said formable platelet gel, said formable platelet gel does not contain thrombin.

3. A formable platelet gel, consisting essentially of: an aqueous suspension of partially frayed Type I fibrillar collagen; calcium chloride; and autologous platelet-rich-plasma, said formable platelet gel does not contain thrombin.

4. A method of making a formable platelet gel, comprising: admixing an aqueous suspension of partially frayed Type I fibrillar collagen, and calcium chloride to form an admixture; adding autologous, platelet-rich-plasma to said admixture in an amount sufficient to produce a formable gel, to produce a platelet mixture; and heating said platelet mixture to produce said formable platelet gel, said formable platelet gel does not contain thrombin.

5. The method of claim 4, further comprising adding particulate bone to said platelet mixture prior to said step of heating.

6. A formable platelet gel produced by the method as claimed in claim 4.

7. A formable platelet gel produced by the method as claimed in claim 5.

8. A method for treating a patient having a bone defect site, comprising: implanting said formable platelet gel as claimed in any one of claims 1, 2, 3, 6, or 7, at said bone defect site in said patient.

* * * * *